US009278193B2

(12) United States Patent
Haider et al.

(10) Patent No.: US 9,278,193 B2
(45) Date of Patent: Mar. 8, 2016

(54) SYSTEMS AND METHODS FOR PROVIDING A CONVECTION-ENHANCED DELIVERY DEVICE

(75) Inventors: M. Ishaq Haider, Cary, NC (US); Frank Martin, Durham, NC (US); Richard Klug, Roxboro, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1151 days.

(21) Appl. No.: 13/143,535

(22) PCT Filed: Jan. 11, 2010

(86) PCT No.: PCT/US2010/020609
§ 371 (c)(1),
(2), (4) Date: Aug. 25, 2011

(87) PCT Pub. No.: WO2010/081067
PCT Pub. Date: Jul. 15, 2010

(65) Prior Publication Data
US 2011/0306934 A1    Dec. 15, 2011

Related U.S. Application Data

(60) Provisional application No. 61/144,023, filed on Jan. 12, 2009.

(51) Int. Cl.
*A61M 25/02* (2006.01)
(52) U.S. Cl.
CPC ......... *A61M 25/02* (2013.01); *A61M 2025/024* (2013.01)

(58) Field of Classification Search
CPC .......... A61M 2025/024; A61M 25/02; A61M 2025/0213; A61M 2025/0266; A61M 2025/0286
USPC ..................... 604/164.04, 174, 178, 179, 180
See application file for complete search history.

(56) References Cited

U.S. PATENT DOCUMENTS

| 5,690,616 A | * | 11/1997 | Mogg | .................... A61M 25/02 128/DIG. 26 |
| 7,270,650 B2 | * | 9/2007 | Morris et al. | .................. 604/177 |
| 7,963,956 B2 | | 6/2011 | Kunst | |

(Continued)

FOREIGN PATENT DOCUMENTS

| DE | 197 49 741 C1 | 11/1998 |
| WO | 01/68180 A1 | 9/2001 |

(Continued)

*Primary Examiner* — Emily Schmidt
*Assistant Examiner* — Lauren M Peng
(74) *Attorney, Agent, or Firm* — J. Timothy Meigs; Craig Metcalf; Kirton McConkie

(57) ABSTRACT

A delivery device system is provided for assisting a patient and physician in maintaining a depth and position of an inserted catheter within a target tissue. The delivery device includes a base member that is secured to an external surface of the patient. The base member includes an aperture through which a catheter is inserted to access the target tissue. The base member further includes a hinged clip that selectively locks into a closed position to secure the catheter within the delivery device and maintain a desired insertion depth of the catheter within the target tissue. The base member further includes a receiving channel for compatibly and adjustably securing an adapter portion of the catheter in a horizontal orientation.

15 Claims, 9 Drawing Sheets

(56) References Cited

U.S. PATENT DOCUMENTS 7,972,305 B2 7/2011 Mittermeyer
2007/0276333 A1* 11/2007 Bierman ................. 604/180

FOREIGN PATENT DOCUMENTS

| WO | 03/068304 A1 | 8/2003 |
| WO | 2004/016309 A2 | 2/2004 |

* cited by examiner

SYSTEMS AND METHODS FOR PROVIDING A CONVECTION-ENHANCED DELIVERY DEVICE

This application is a National Stage of International Application No. PCT/US2010/020609, filed Jan. 11, 2010, and entitled SYSTEMS AND METHODS FOR PROVIDING A CONVECTION-ENHANCED DELIVERY DEVICE which claims the benefit of U.S. Provisional Application No. 61/144,023, filed Jan. 12, 2009. This application claims priority to and incorporates herein by reference the above-referenced applications in their entirety.

BACKGROUND OF THE INVENTION

The present invention relates to a convection-enhanced delivery system for use in any targeted drug delivery procedure including convection-enhanced delivery (CED) and chronic intracranial administrations. CED is the continuous injection under positive pressure of a fluid containing a therapeutic agent. This technique is especially useful for administering therapeutic agents to tissues that are inaccessible via traditional oral medications or venous infusion techniques. For example, for central nervous system (CNS) applications, drug delivery by systemic or by intrathecal methods is not very effective because of the blood-brain bather and limitations with regard to the drug diffusion into the tissue. At best, traditional methods of treatment result in incomplete, non-targeted and heterogeneous dispersion throughout the CNS.

CED may be used to overcome some of the restrictions associated with traditional and other delivery systems. CED utilizes a pressure gradient to infuse substances directly into the interstitial space of a target tissue, for example a solid tumor tissue, via a catheter. This process is known as interstitial infusion and relies on bulk, convective flow and can be used to distribute both small and large molecular weight substances over clinically relevant volumes within solid tissue. Additional benefits include the ability to deliver the therapeutic at relatively constant concentrations throughout the volume of distribution.

The ability to accurately position the catheter within the target tissue is a difficult challenge requiring precise instrumentation and experienced hands. Once the catheter is accurately inserted to a desired depth, the position of the catheter must remain steady so as to ensure effective dispersion of the medicament within the target tissue. The catheter commonly remains inserted within the target tissue for weeks or months at a time to facilitate extended treatment times and the multiple treatment sessions required to achieve adequate tissue therapy. The patient must therefore be extremely cautious to prevent disruption of the catheter between, and during treatment sessions. Bandages, protective shells and the like are commonly used to assist the patient in maintaining the position of the catheter. However these methods are unsightly and inconvenient for the patient. Thus, while methods currently exist for maintaining the inserted position of CED catheters, challenges still exist. Accordingly, there is a need in the art for a delivery device system that is effective and convenient in assisting a patient in maintaining an inserted CED catheter without the drawbacks of currently available methods. Such a delivery device system is disclosed herein.

BRIEF SUMMARY OF THE INVENTION

The present invention relates to a convection-enhanced delivery system for use in any targeted drug delivery procedure including convection-enhanced delivery (CED) and chronic intracranial administrations. Specifically, the present invention provides a delivery device that includes a generally planar mounting surface for attaching the delivery device to an external surface of a patient. In some embodiments, a target tissue of the patient is first accessed by providing an aperture in the patient via a drill bit or burr. The delivery device is then positioned on the patient such that an aperture in the base member is centered on top of the access aperture of the patient. The delivery device is then secured to the external surface of the patient via a plurality of fasteners, such as screws or an adhesive. The aperture of the base member provides a pathway through the base member through which a catheter is inserted to access the target tissue of the patient, via the patient aperture.

The base member further includes a hinged clip that selectively moves between an opened position and a closed position. The opened position of the hinged clip exposes the aperture through the base thereby enabling a catheter to be inserted through the aperture and into the target tissue to a desired insertion depth. Once the desired insertion depth is attained, the hinged clip is selectively moved to and locked in a closed position to secure the insertion depth of the catheter in the target tissue. Additionally, the closed position of the hinged clip repositions an adapter portion of the catheter from a vertical orientation to a horizontal orientation. The horizontal orientation reduces the distance between the adapter portion of the catheter and the patient, thereby reducing the vertical profile of the delivery device and inserted catheter.

The base member further includes a receiving channel for receiving and securing the adapter portion of the catheter when the delivery device is in a closed position. An inner surface of the receiving channel may include features for adjustably interacting with an outer surface of the catheter adapter. For example, in some implementations of the present invention the inner surface of the receiving channel includes a plurality of tongues that fit within a plurality of grooves located on an external surface of the catheter adapter. In other implementations the inner surface of the receiving channel includes a contour or feature that mirrors an external surface of the catheter adapter. The interaction of the receiving channel and the catheter adapter retain the catheter adapter within the receiving channel at various positions within the receiving channel. In some implementations of the present invention, the insertion depth of the catheter in the target tissue is adjusted by selectively positioning the catheter adapter within the receiving channel. In other implementations, compatible features between abutting surfaces of the receiving channel and the catheter adapter enable precise and predetermined insertion depths of the catheter within the target tissue.

In some embodiments a semi-flexible, metallic catheter is used in conjunction with the delivery device. In other embodiments a flexible, polymer based catheter is used with the delivery device, thereby requiring the use of a trocar or introducer needle to insert the catheter into the target tissue. In some implementations of the present invention, a micromanipulator is coupled to a portion of the catheter adapter to provide control and accuracy for insertion of the catheter into the target tissue.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illus

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
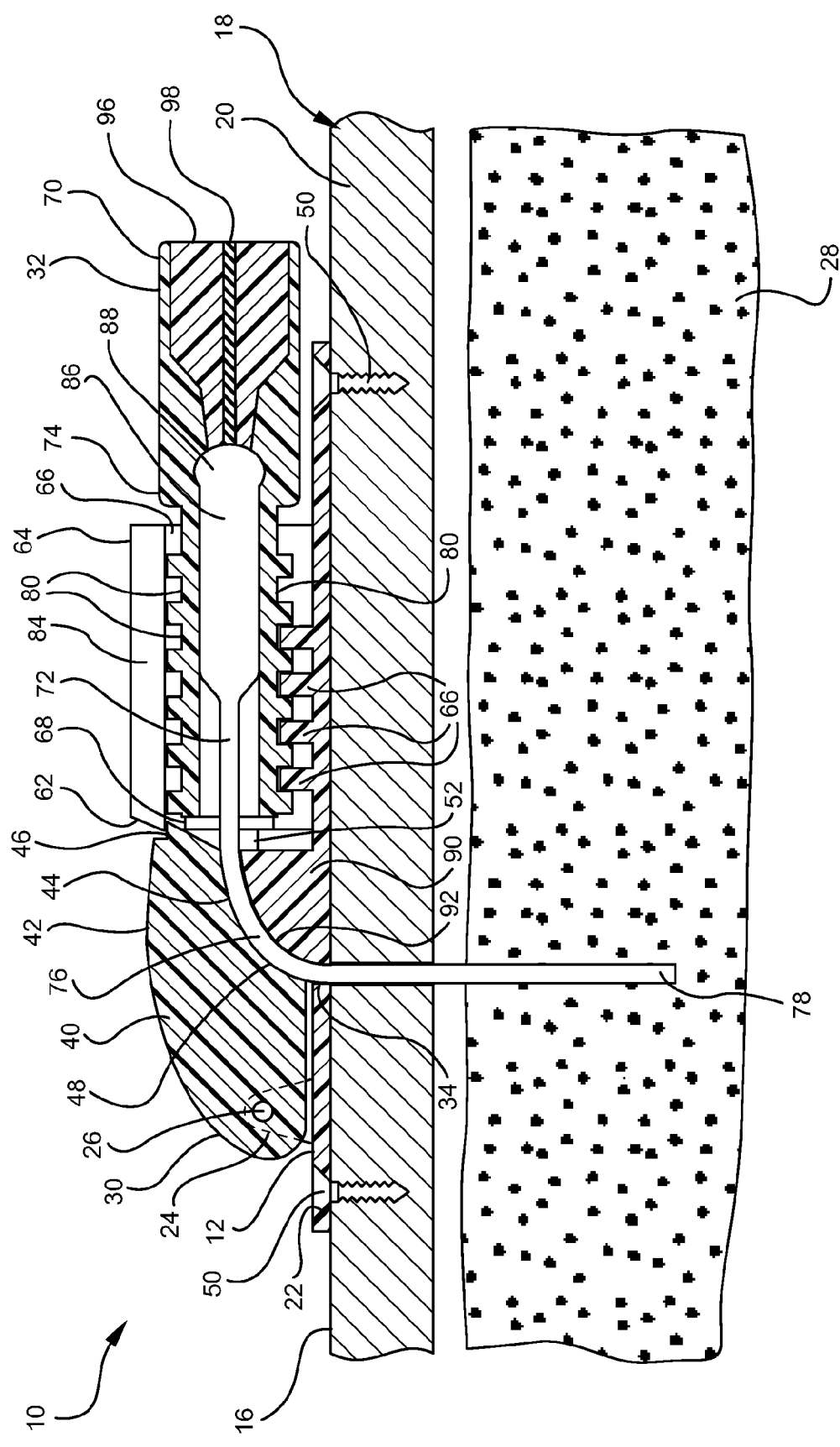
- FIG. 1 is a cross-sectional view of an implementation of a convection-enhanced delivery device and inserted catheter in a closed position.

Referring now to FIG. 1, a convection-enhanced delivery system 10 is shown. The delivery system 10 comprises a base 12 that includes a generally planar mounting surface 14 that interfaces directly with an outer surface 16 of a patient 18. In some embodiments, the mounting surface 14 of the base 12 is arched or otherwise shaped to conform to a non-planar external surface 16. In other embodiments, a non-planar external surface 16 is made planar by removing excess external surface 16 material. Once the external surface 16 is made planar, the planar mounting surface 14 is positioned on the external surface 16 and secured thereto via a plurality of fasteners 50. In other embodiments, the base 12 comprises a flexible or semi-rigid material that contours to the non-planar external surface 16. For these embodiments, the base portion 12 of the delivery device 10 is contoured and held in a contoured configuration by securing the device 10 to the external surface 16 via the plurality of fasteners 50.

The plurality of fasteners 50 may include any device or combination of devices sufficient to maintain an interface between the base 12 and the external surface 16 of the patient 18. For example, in some embodiments the plurality of fasteners 50 comprises bone screws. In other embodiments, the plurality of fasteners 50 comprises an adhesive, such as an epoxy, or an adhesive strip (not shown). In some embodiments, the delivery device 10 is attached directly to the bone 20 of the patient 18 via fasteners 50. In other embodiments, the delivery device 10 is placed directly on the dermis (not shown) of the patient 18 and secured to the patient 18 via fasteners 50 that are anchored into the bone 20. The fasteners 50 are generally inserted through an aperture 22 of the base, wherein a head portion of the fastener 50 binds on a chamfered surface of the aperture 22 to secure the position of the delivery device 10.

Figure 7:
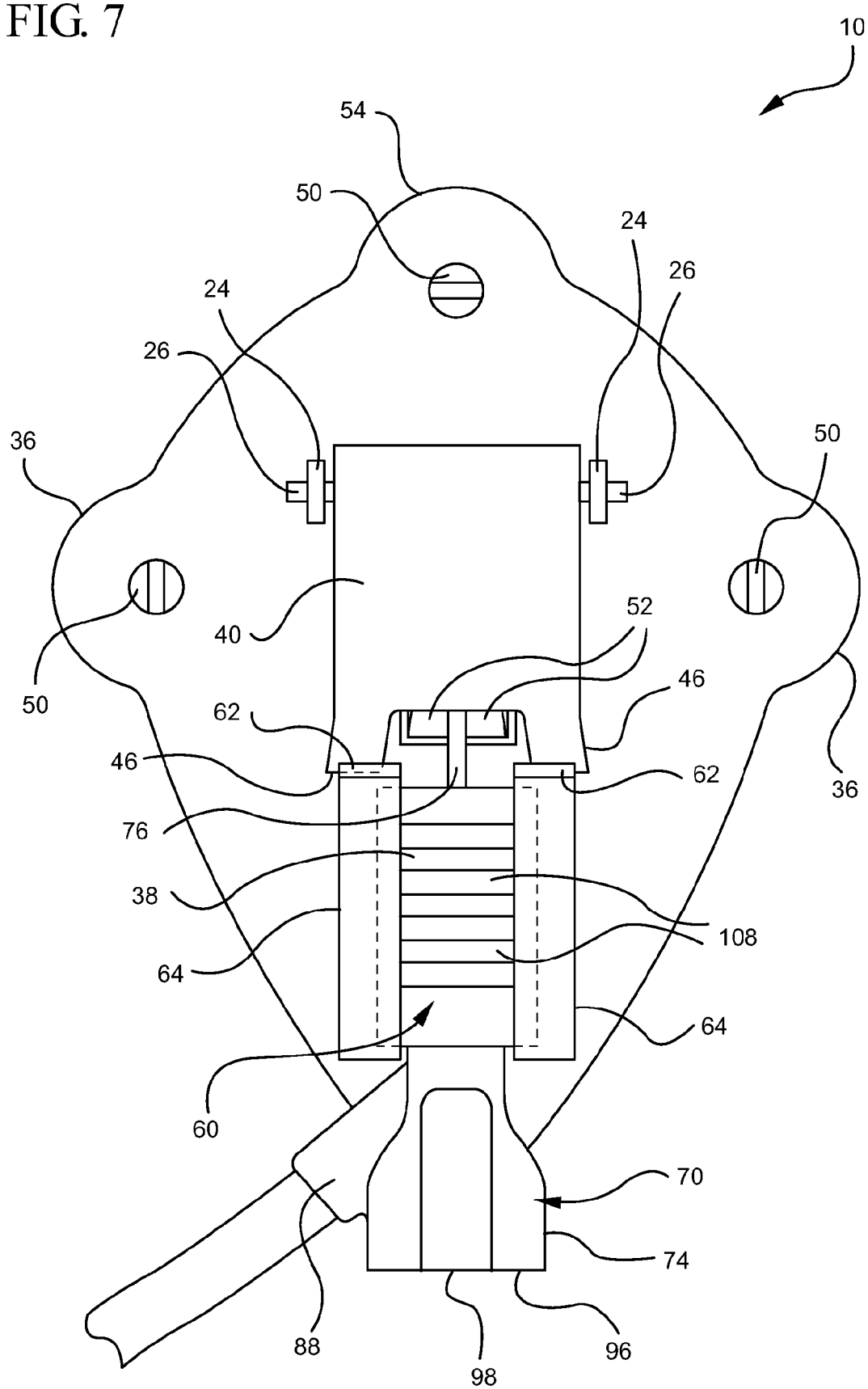
FIG. 7 is a perspective top view of an implementation of a convection-enhanced delivery device and inserted catheter in a closed position.

A proximal end 30 of the base 12 further comprises a hinged clip 40. The clip 40 is hingedly anchored to the base 12 via a stationary stator 24 and pin 26. The clip 40 further comprises an outer surface 42 and an inner surface 44. The outer surface 42 may comprise any shape or contour that maintains a low profile when the clip 40 is in a closed position, as illustrated in FIG. 1. In some embodiments, the outer surface 42 is gently arched and is free from sharp edges that may snag or otherwise catch on clothing or hair of the patient 18. In other embodiments, the outer surface 42 further comprises a ledge feature 46 for interlockedly coupling with a clip catch 62 feature of the delivery device 10. The coupling of the ledge feature 46 and the clip catch 62 hold the clip 40 in a closed and locked position, as shown in FIGS. 1 and 7.

The inner surface 44 is generally contoured to form an arched surface 48. The radius of the arched surface 48 is selected to provide a gentle angle by which an uninserted portion 76 of a catheter 72 is bent in a non-occluding manner. The base 12 further comprises a catheter support 90 having a contoured support surface 92 that mirrors the arched surface 48 of the clip 40. As such, the uninserted portion 76 of the catheter 72 is interposedly held between the clip 40 and the catheter support 90 at a desired radial (angle). When in the closed position, the clip 40 and the catheter support 90 assist to maintain the position of the inserted portion 78 of the catheter 72 within the target tissue 28. Additionally, in some embodiments the outer surface 42 of the clip 40 further comprises a pair of catheter guards 52 that straddle an unsupported portion of the catheter 76. The catheter guards 52 generally comprise a gap interposed between the two guards 52 into which a portion of the uninserted portion 76 of the catheter 72 is inserted upon positioning the clip 40 in a closed configuration. The catheter guards 52 thus hold the uninserted portion 76 of the catheter 72 to prevent lateral movement of the catheter 76 with respect to the clip 40 and catheter support 90.

Figure 3:
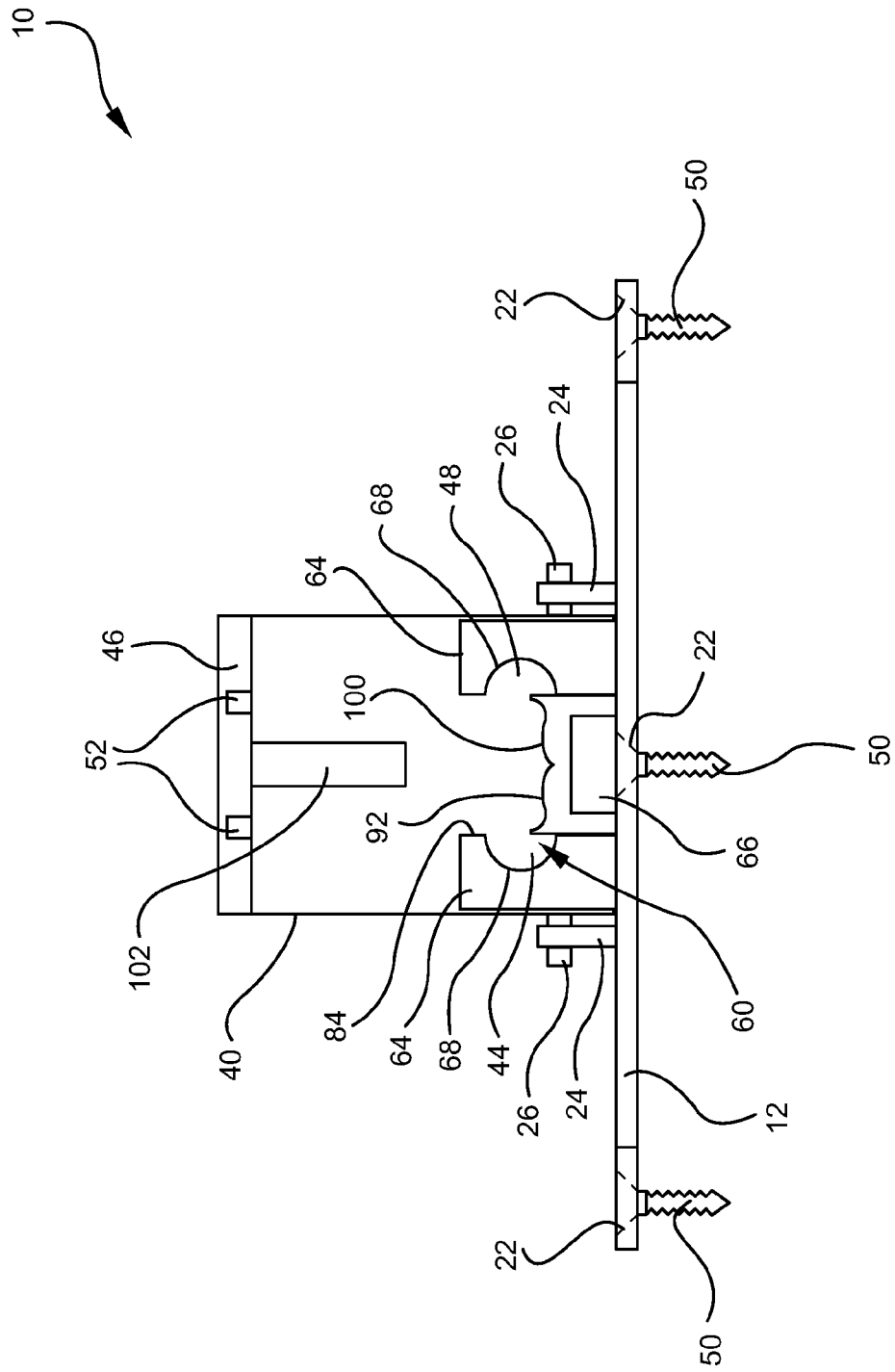
FIG. 3 is a plan end view of an implementation of a convection-enhanced delivery device in an opened position.
Figure 6:
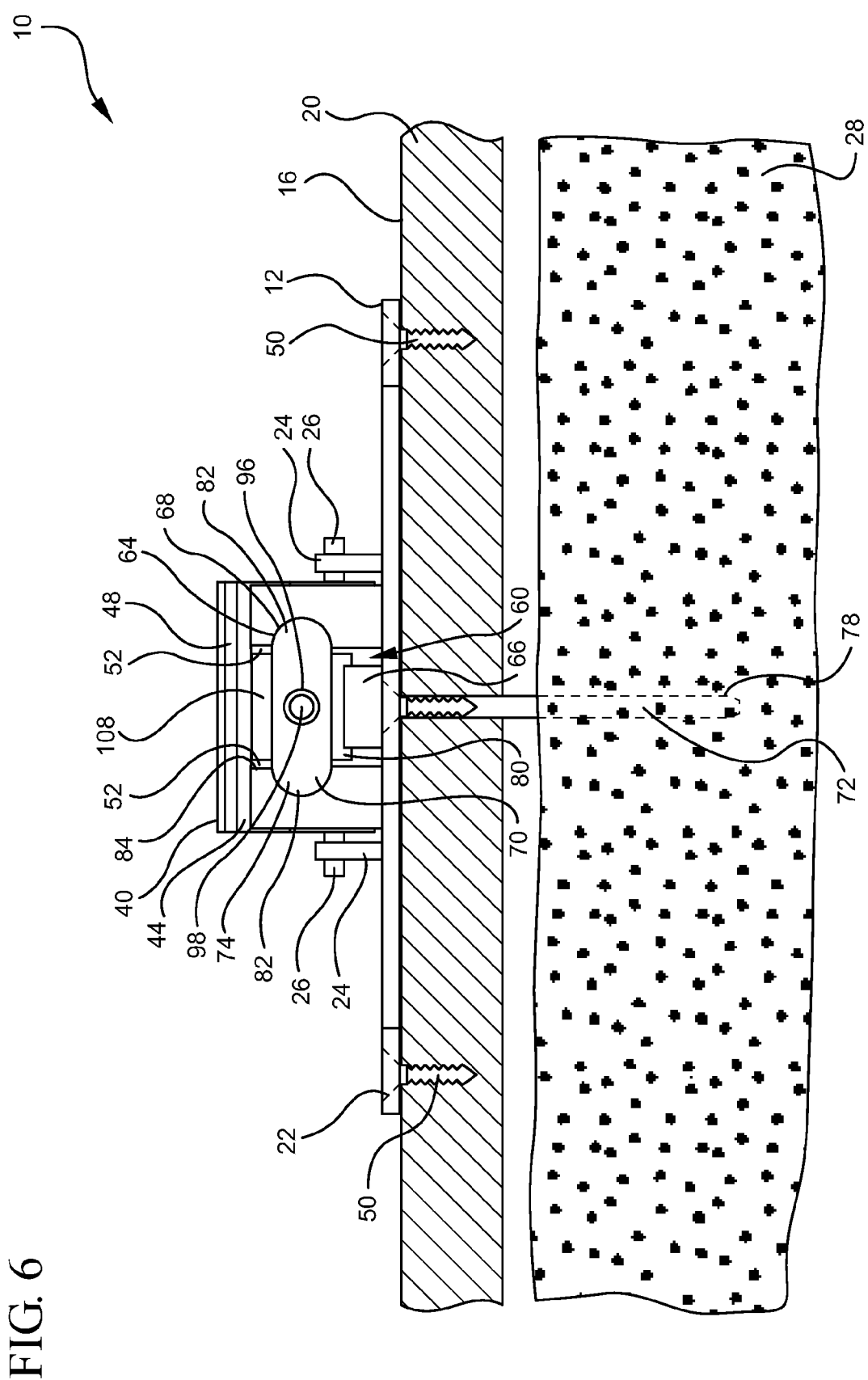
FIG. 6 is a cross-sectioned rear view of an implementation of a convection-enhanced delivery device in an opened position following insertion of a catheter assembly.
Figure 8:
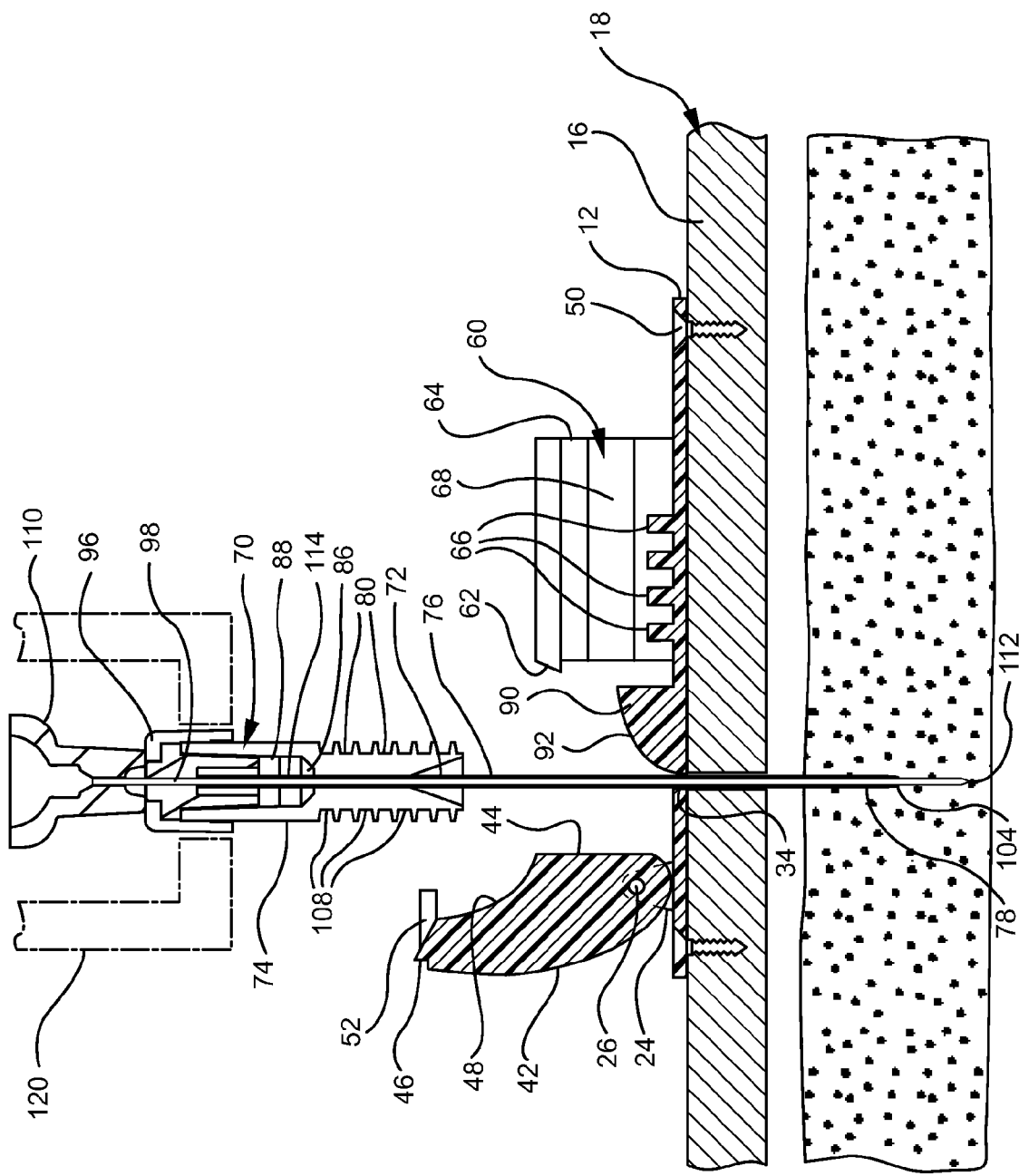
FIG. 8 is a cross-sectioned side view of an implementation of a convection-enhanced delivery in an opened position and during insertion of a catheter into a target tissue.

A distal end 32 of the base further comprises a receiving channel 60. The receiving channel 60 generally comprises a pair of opposing walls 64 that attach to the base 12 to provide a three-sided channel. The opposing walls 64 are generally parallel and spaced apart so as to accommodate insertion of a catheter adapter 74 therein. In some embodiments, an inner surface of the opposing walls 64 is recessed 68 or otherwise contoured to compatibly receive an outwardly extended surface 82 of the catheter adapter 74, as illustrated in FIGS. 3, 6, and 8. In other embodiments, a portion of the inner surface of the opposing walls 64 is extended inwardly into the channel 60 to provide a lip 84. The opposing lips 84 generally provide an opening to the channel 60 that is slightly narrower than the width of the catheter adapter 74. Thus, in some embodiments the outer surface of the catheter adapter 74 contacts the opposing lips 84 to outwardly bias the opposing walls 64 during insertion of the catheter adapter 74 within the channel 60. Once the catheter adapter 74 is positioned within the receiving channel 60, the opposing walls 64 are no longer outwardly biased, and the opposing lips 84 are repositioned to overlap the catheter adapter 74 to retain the adapter 74 within the channel 60.

The portion of the channel 60 defined by the base 12 further comprises a plurality of tongues 66 extending upwardly from the base 12. The plurality of tongues 66 provide a spaced surface which is adjustably fitted into a plurality of grooves 80 located on a catheter adapter portion 74 of a catheter assembly 70. The interaction between the plurality of tongues 66 and the plurality of grooves 80 enables varied placement of the catheter adapter 74 within the receiving channel 60. As such, the insertion depth of the inserted portion 78 of the catheter 72 is determined by the position of the catheter adapter 74 within the receiving channel 60.

The catheter adapter 74 of the catheter assembly 70 further includes a fluid chamber 86 and fluid inlet 88, as is conventional with intravenous catheters. Other features of the catheter adapter 74 include a plug 96 and a sealed pathway 98 through which a trocar 110 or introducer needle is inserted, in some embodiments (see FIG. 8). For example, in some embodiments the catheter 72 material is a semi-flexible polymer material that does not possess sufficient rigidity to pierce the target tissue 28. For these embodiments, a trocar 110 is first inserted through the catheter 72 via the pathway 98 of the plug 96. The trocar 110 and catheter 72 are then inserted through an aperture 34 of the base 12 and into the target tissue 28 to a desired insertion depth. Once the desired insertion depth is attained, the clip 40 is pivoted to a closed position and secured therein via the coupling of the ledge feature 46 and the clip catch 62. The adapter portion 74 of the catheter assembly 70 is then secured in the receiving channel 60, and the trocar 110 is removed from the catheter assembly 70. At this point, a fluid or medicament is administered to the target tissue 28 via the fluid inlet 88.

In other embodiments, the catheter 72 material is a semi-flexible metal material that possesses sufficient rigidity to pierce the target tissue 28. For these embodiments, use of a trocar 110 or introducer needle is unnecessary and therefore the catheter adapter 74 may be modified to exclude the plug 96 and sealed pathway 98. Still, in other embodiments the size or gauge of the metal catheter 72 may still require the use of a trocar 110 to enable accurate and efficient placement of the catheter 72 within the target tissue 28.

Figure 2:
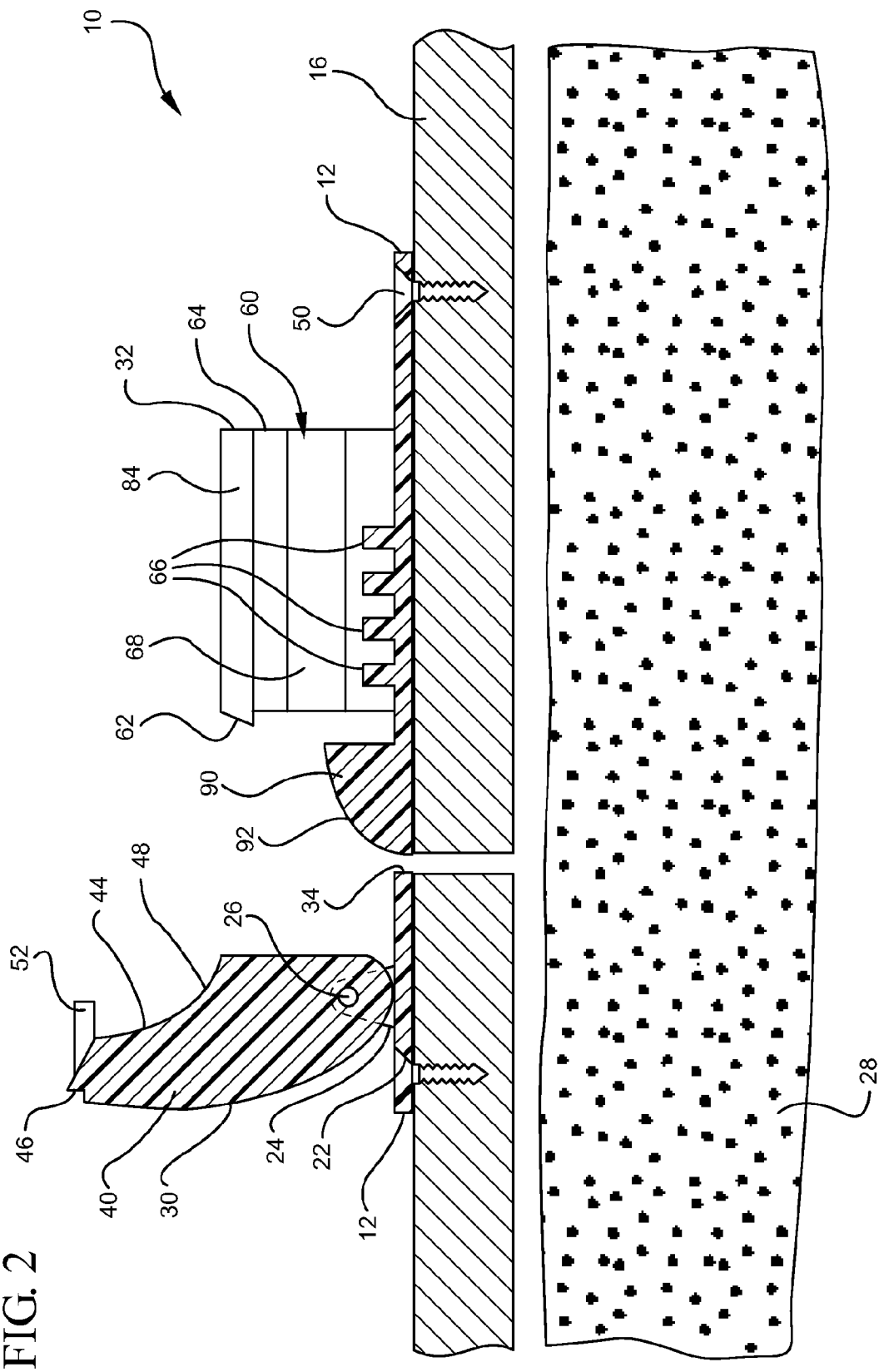
FIG. 2 is a cross-sectional side view of an implementation of a convection-enhanced delivery device in an opened position.

Referring now to FIG. 2, a cross-sectioned side view of the delivery system 10 is shown in an opened position. The aperture 34 of the base 12 is generally positioned adjacent to the catheter support 90, such that the support surface 92 ends into the aperture 34. As such, a catheter 72 may be supported by the catheter support 90 and inserted directly into the aperture 34 without kinking or otherwise occluding the catheter 72. Additionally, the walls of the aperture 34 are generally perpendicular to the base 12 so as to direct the inserted portion 78 of the catheter 72 into the target tissue 28 at a right angle. In some embodiments, the aperture 32 is provided at an angle of less than 90°, such that the catheter 72 is inserted into the target tissue 28 at an angle of less than 90°.

Referring now to FIG. 3, a perspective view of the distal end 32 of the delivery system 10 is shown in an opened position. In some embodiments, the support surface 92 of the catheter support 90 further includes a groove 100 to compatibly receive an outer surface of the uninserted portion 76 of the catheter 72. The groove 100 generally includes a recessed feature having a radius or contour configured to retain the catheter 72 on the support surface 90. In other embodiments, the arched surface 48 of the clip 40 further comprises a groove 102 to compatibly receive an outer surface of the uninserted portion 76 of the catheter 72. The groove 102 generally includes a recessed feature having a radius or contoured configured to retain the catheter 72 in a desired position between the clip 40 and the catheter support 90. In some embodiments, the grooves 100 and 102 are used in combination to further retain a desired position of the catheter 72 between the clip 40 and the catheter support 90.

Figure 4:
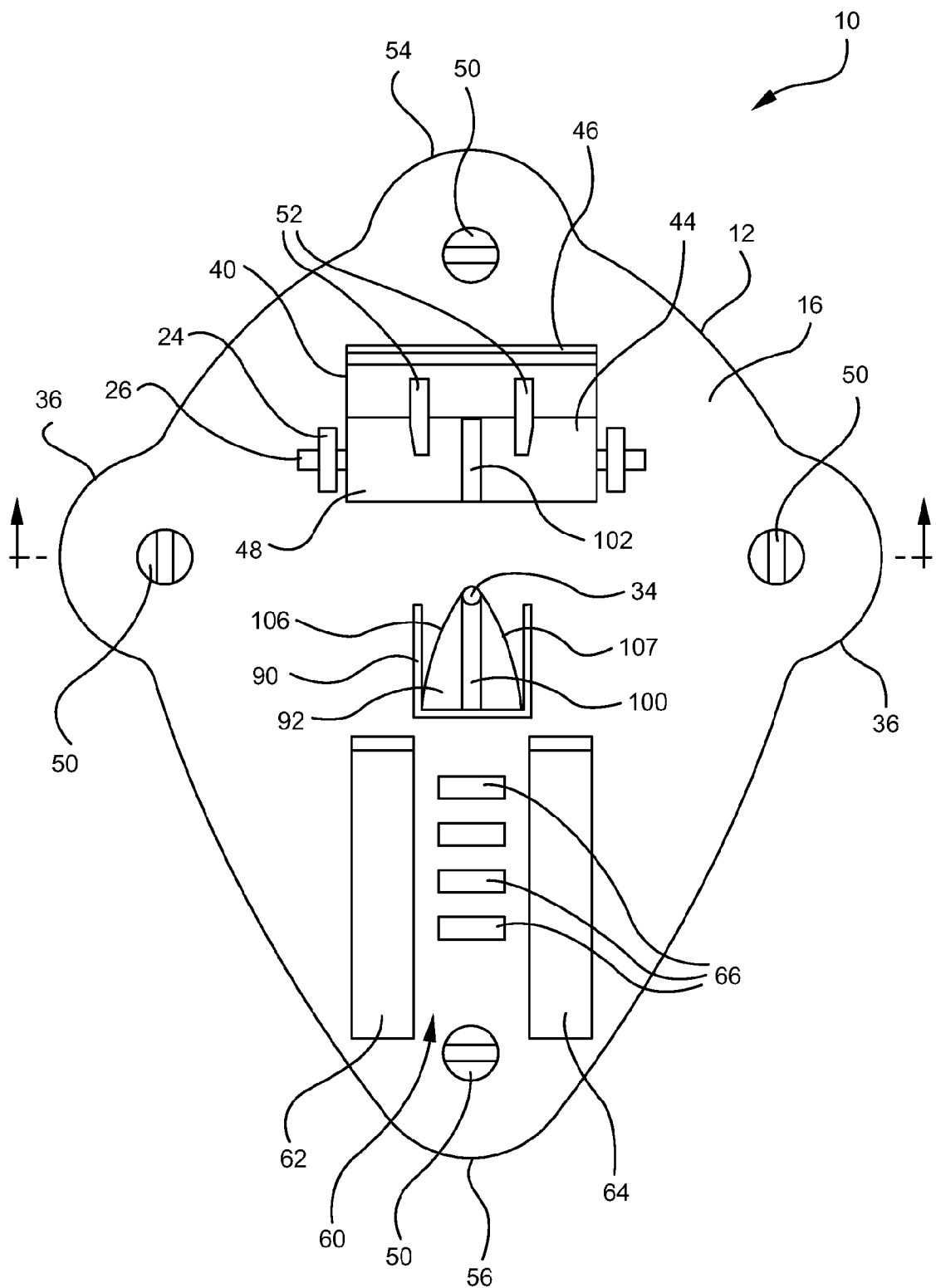
FIG. 4 is a top plan view of an implementation of a convection-enhanced delivery device in an opened position.

Referring now to FIG. 4, a perspective top view of the delivery device 10 is shown in an opened configuration. In some embodiments, the support surface 92 of the catheter support 90 further comprises a tapered slope 106 that directs and guides the catheter 72 over the support surface 92 and into the aperture 34. In other embodiments, the support surface 92 is funnel-shaped such that the tapered walls 107 of the support surface 92 direct the catheter 72 into the aperture 34. The base 12 of the delivery device 10 may further include features to promote stability to the mounted device 10. For example, in some embodiments lateral protrusions or wings 36 are provided to accommodate a fastener, as well as to provide lateral stability to the device 10. In other embodiments, forward and aft wings 54 and 56 are provided to further stabilize the mounted delivery device 10.

Figure 5:
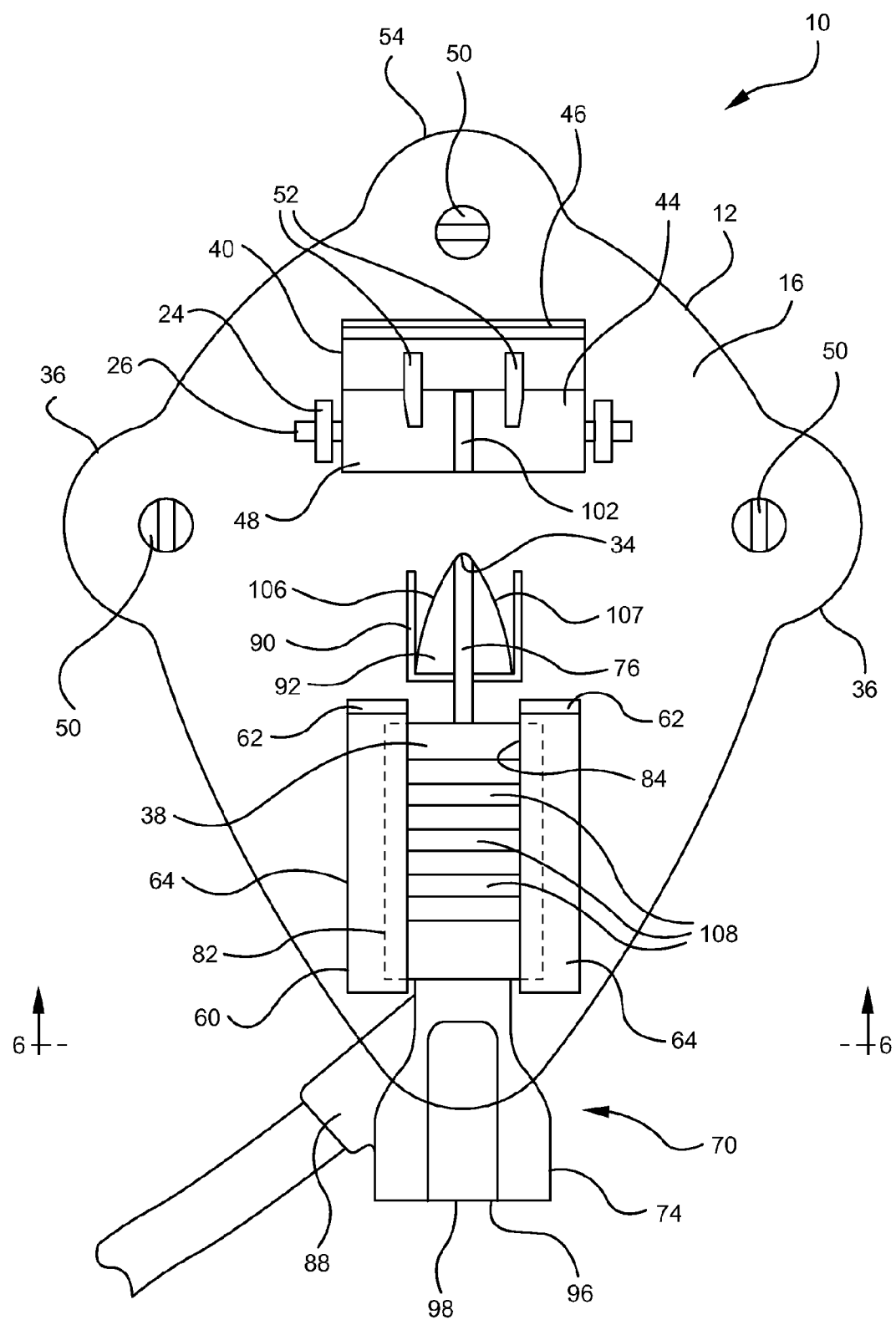
FIG. 5 is a top plan view of an implementation of a convection-enhanced delivery device in an opened position following insertion of a catheter assembly.

Referring now to FIG. 5, a perspective top view of the delivery device 10 is shown in an opened configuration following insertion of a catheter assembly 70. The catheter adapter 74 of the catheter assembly 70 is positioned and secured in the receiving channel 60. As such, the position of the catheter 76 is maintained in the aperture 34 and in the target tissue 28. The position of the catheter adapter 74 within the channel 60 is maintained by an interaction between the plurality of tongues 66 (see FIG. 4) of the channel 60 and the plurality of grooves 80 adjacent to the plurality of tongues 66 (see FIG. 1). The interaction between the plurality of tongues 66 and the plurality of grooves 80 prevents the catheter adapter 74 from sliding within the channel 60. Additionally, lip portions 84 of the opposing walls 64 overlap a portion of the upper surface 38 of the catheter adapter 74 to further retain the catheter adapter 74 within the channel 60. Furthermore, in some embodiments the upper surface 38 of the catheter adapter 74 includes a second plurality of grooves 108. For these embodiments, the catheter adapter 74 may be rotated and positioned within the channel 60 such that the upper surface 38 of the catheter adapter 74 forms an interface with the plurality of tongues 66. As such, the position of the fluid inlet 88 may be adjusted as required by the physician.

Referring now to FIG. 6, a cross-sectioned rear view of the delivery device 10 is shown in an opened configuration following insertion of a catheter assembly 70. FIG. 6 clearly demonstrates the interaction between the catheter adapter 74 and the groove 68 or recessed feature of the opposing walls 64 and the lips 84. Additionally, the plurality of grooves 80 and the plurality of tongues 66 are clearly shown in a coupled configuration. In some embodiments, the catheter adapter 74 comprises a plurality of tongues that adjustably couple with a plurality of grooves within the channel 60 to secure the position of the catheter adapter 74 within the channel 60. One of skill in the art will appreciate that any adjustable coupling system may be used to position the catheter adapter 74 within the channel 60 so as to maintain a position of the catheter 72 within the target tissue 28.

Referring now to FIG. 7, a perspective top view of the delivery device 10 is shown in a closed position. The clip 40 of the device 10 has been moved to a closed position such that the ledge features 46 of the clip 40 have interlocked with the clip catch features 62 of the opposing walls 64. As a result, the catheter guards 52 have been repositioned to straddle a portion of the uninserted catheter 76. Thus, the positions of the catheter guards 52, the clip 40 and the catheter support 90 (not seen in this Figure) secure the position of the catheter 72 relative to the delivery device 10. Additionally, the arched position of the catheter 72 and the horizontal position of the catheter adapter 74 provide a low profile delivery system 10. Once the catheter 72 and catheter adapter 74 have been positioned and secured within the delivery system 10, a fluid or medicament is then infused into to the target tissue 28 via the fluid inlet 88 and the inserted portion 78 of the catheter 72.

Referring now to FIG. 8, a cross-sectioned side view of the delivery system 10 is shown following insertion of the catheter 78 into a target tissue 28. In some embodiments, insertion of the catheter 78 into a target tissue 28 requires the assistance of a trocar 110 or an introducer needle (not shown). The trocar 110 generally comprises a semi-rigid wire 114 or stylet having a length that extends through an internal cavity of the catheter assembly 70. The trocar 110 further comprises a tip end 112 that extends beyond a tip portion 104 of the catheter 78. The tip end 112 is generally sharpened or tapered to facilitate movement of the tip end 112 and the tip portion 104 of the catheter through the target tissue 28. The trocar 110 and catheter 78 are inserted into the target tissue 28 until a desired insertion depth is attained. In some embodiments, a mechanical device such as a micromanipulator 120 (shown in phantom) is coupled to the catheter adapter 74 to assist in placement of the catheter 78 and trocar 110 within the target tissue 28. Once the desired insertion depth is attained, the uninserted portion 76 of the catheter is arched over the support surface 92 of the catheter support 90 and the catheter adapter 74 is secured within the receiving channel 60. The clip 40 is then moved to a closed position, and the ledge features 46 interlock with the clip catches 62 of the opposing walls 64. The trocar 110 is then removed from the catheter assembly 70 thereby enabling infusion to the target tissue via the fluid inlet 88. In some embodiments, the trocar 110 is removed prior to moving the clip 40 to a closed position. Following removal of the trocar 110, the clip 40 is moved to a closed position enabling infusion to the target tissue via the fluid inlet 88.

In some embodiments, multiple insertion depths are achieved with a single catheter assembly 70. For example, in some embodiments a catheter assembly 70 having a catheter length is inserted into the target tissue to a first depth wherein the catheter adapter 74 is secured within the receiving channel 60 in a first position. In some embodiments, the insertion depth of the catheter 72 is increased by repositioning the catheter adapter 74 within the receiving channel 60 to a second position. Likewise, in other embodiments the insertion depth of the catheter 72 is decreased by reposition the catheter adapter 74 within the receiving channel 60 to a third position. In other embodiments, the insertion depth of the catheter 78 is adjusted by providing a plurality of catheter assemblies, each assembly 70 having a catheter 72 comprising a different length. Thus, for those embodiments requiring a greater insertion depth, a catheter assembly 70 having a catheter 72 with a greater length is selected. Likewise, for those embodiments requiring a lesser insertion depth, a catheter assembly 70 having a catheter 72 with a lesser length is selected.

Figure 9:
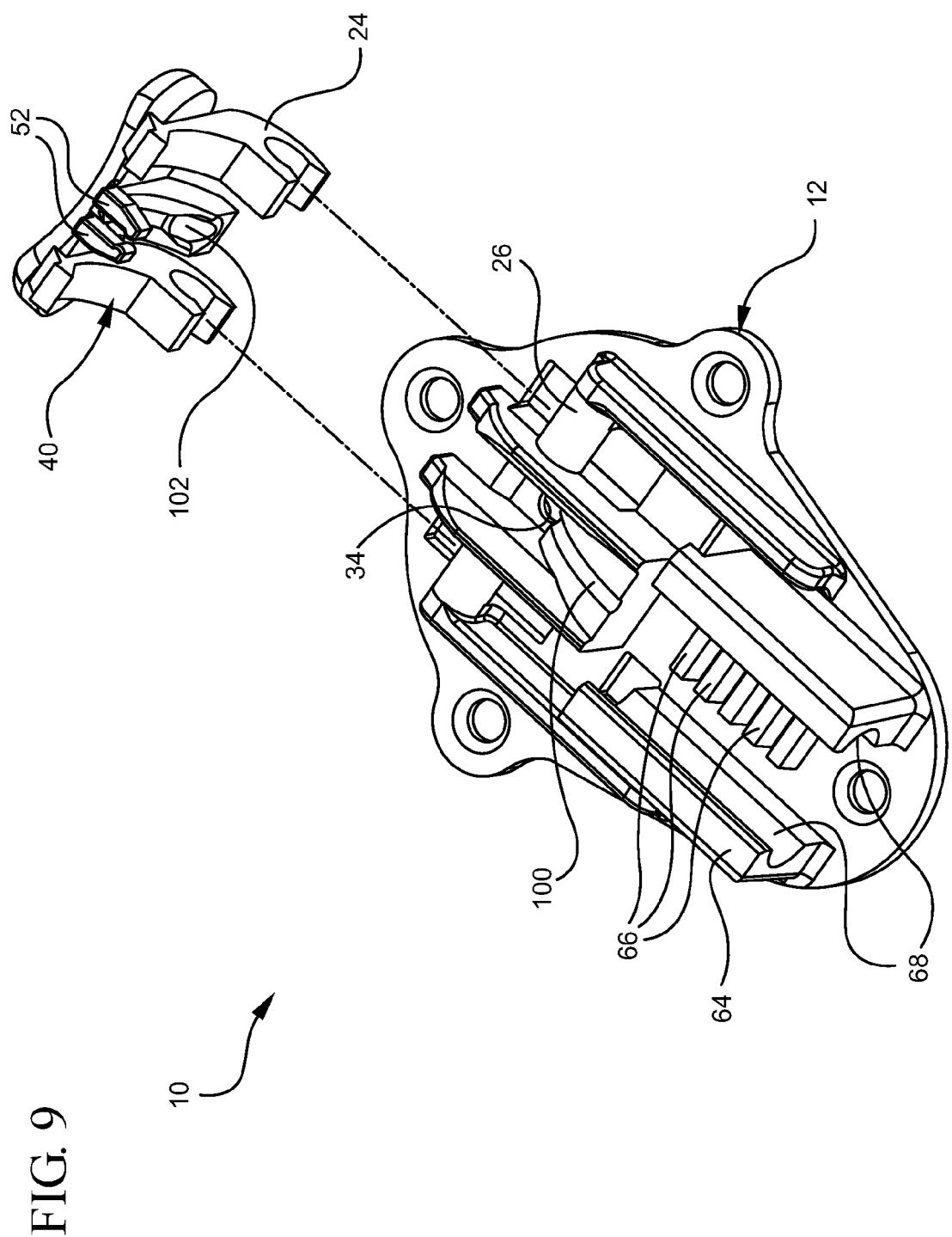
FIG. 9 is an exploded, perspective view of an implementation of a convection-enhanced delivery device in accordance with a representative embodiment of the present invention.

Referring now to FIG. 9, an alternative embodiment of the present invention is shown. The delivery system 10 may be modified to include a removable clip 40. Other design features may be further modified to optimize functionality of the system 10. For example, in some embodiments base 12 is modified to include a slightly concave surface configured to more accurately interface with a non-planar surface, such as the surface of a patients scalp. In other embodiments, delivery system 10 is modified to include additional structural features to provide support to the various functional features of the device, as shown.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A catheter system, comprising:
   a catheter adapter from which a catheter extends, the catheter adapter including a plurality of tongues formed on an outer surface of the catheter adapter, and
   a mounting apparatus for maintaining a position of the catheter adapter to thereby maintain a depth of insertion of the catheter, the mounting apparatus comprising:
   a base having a substantially planar surface for forming an interface with a patient;
   a receiving channel forming a distal end of the base and configured to receive the catheter adapter, the receiving channel including a plurality of grooves configured to interlock with the plurality of tongues when the catheter adapter is contained within the receiving channel at a plurality of positions, a portion of the receiving channel further forming a clip catch;
   a catheter support having a first cambered surface and a first groove for receiving the catheter when the catheter adapter is received within the receiving channel at any of the plurality of positions;
   an aperture positioned proximal to the catheter support, the aperture providing a pathway through the base to accommodate passage of the catheter through the base and into the patient when the catheter adapter is received within the receiving channel such that the position of the catheter adapter within the receiving channel defines a depth to which the catheter extends into the patient;
   a clip hingedly coupled to a proximal end of the base such that the clip pivots between an open position and a closed position, the clip having an inner surface and an outer surface, the inner surface having a second cambered surface and a second groove for retaining the catheter against the first cambered surface and the first groove when the clip is in the closed position, the outer surface having a ledge feature to compatibly interlock with the clip catch to secure the clip in the closed position.

2. The apparatus of claim 1, wherein the receiving channel is formed by a pair of opposing walls spaced to receive the catheter adapter.

3. The apparatus of claim 2, wherein each wall includes an inwardly extending lip at an upper edge of the wall, a distance between the two lips being less than a width of the catheter adapter, the walls being configured to bias outwardly to enable the catheter adapter to pass between the lips and into the receiving channel, the walls further being configured to return to an unbiased position after the catheter adapter is positioned within the receiving channel such that the lips are positioned partially above the catheter adapter when the walls are in the unbiased positioned thereby maintaining the catheter adapter within the receiving channel.

4. The apparatus of claim 2, wherein the clip catch is formed on a proximal end of each wall.

5. The apparatus of claim 1, wherein the clip further comprises a pair of opposing catheter guards that are positioned distal to the catheter support when the clip is in the closed position, the catheter guards being configured to straddle a portion of the catheter when the clip is in the closed position.

6. The apparatus of claim 1, wherein the base further comprises a plurality of holes for receiving a plurality of fasteners.

7. The apparatus of claim 1, further comprising a trocar configured to insert within a distal end of the catheter adapter, the trocar having a length sufficient to extend out through a proximal end of the catheter to enable the trocar and the catheter to be inserted through the aperture and into the patient.

8. A method for maintaining a depth of insertion of a catheter comprising:
attaching a mounting apparatus to a patient, the mounting apparatus comprising:
a base having a substantially planar surface for forming an interface with the patient;
a receiving channel forming a distal end of the base and configured to receive a catheter adapter from which the catheter extends, the receiving channel including a plurality of grooves configured to interlock with a plurality of tongues formed on the catheter adapter when the catheter adapter is contained within the receiving channel at a plurality of positions, a portion of the receiving channel further forming a clip catch;
a catheter support having a first cambered surface and a first groove for receiving the catheter when the catheter adapter is received within the receiving channel at any of the plurality of positions;
an aperture positioned proximal to the catheter support, the aperture providing a pathway through the base to accommodate passage of the catheter through the base and into the patient when the catheter adapter is received within the receiving channel such that the position of the catheter adapter within the receiving channel defines a depth to which the catheter extends into the patient; and
a clip hingedly coupled to a proximal end of the base such that the clip pivots between an open position and a closed position, the clip having an inner surface and an outer surface, the inner surface having a second cambered surface and a second groove for retaining the catheter against the first cambered surface and the first groove when the clip is in the closed position, the outer surface having a ledge feature to compatibly interlock with the clip catch to secure the clip in the closed position;
inserting the catheter through the aperture and into the patient;
positioning the catheter between the first and second grooves while also positioning the catheter adapter within the receiving channel at one of the plurality of positions by interlocking the grooves and tongues such that the catheter is inserted into the patient to a corresponding depth and such that the interlocked grooves and tongues maintain the position of the catheter adapter and therefore maintain the corresponding depth of the catheter.

9. The method of claim 8, wherein the receiving channel is formed by a pair of opposing walls spaced to receive the catheter adapter, and wherein each wall includes an inwardly extending lip at an upper edge of the wall, a distance between the two lips being less than a width of the catheter adapter, the walls being configured to bias outwardly to enable the catheter adapter to pass between the lips and into the receiving channel, the walls further being configured to return to an unbiased position after the catheter adapter is positioned within the receiving channel such that the lips are positioned partially above the catheter adapter when the walls are in the unbiased positioned thereby maintaining the catheter adapter within the receiving channel.

10. The method of claim 8, wherein the clip further comprises a pair of opposing catheter guards that are positioned distal to the catheter support when the clip is in the closed position, the catheter guards being configured to straddle a portion of the catheter when the clip is in the closed position.

11. The method of claim 8, wherein the clip catch is formed on a proximal end of each wall.

12. The method of claim 8, wherein attaching the mounting apparatus to the patient comprises inserting bone screws through the base and into one or more bones of the patient.

13. A catheter system, comprising:
a catheter adapter from which a catheter extends, the catheter adapter including a plurality of tongues formed on an outside surface of the catheter adapter; and
a mounting apparatus for maintaining a position of the catheter adapter to thereby maintain a depth of insertion of the catheter, the mounting apparatus comprising:
a base for forming an interface with a patient;
a receiving channel forming a distal end of the base and configured to receive the catheter adapter, the receiving channel including a plurality of grooves configured to interlock with the plurality of tongues when the catheter adapter is contained within the receiving channel at a plurality of positions;
a catheter support having a first cambered surface and a first groove for receiving the catheter when the catheter adapter is received within the receiving channel at any of the plurality of positions;
an aperture positioned proximal to the catheter support, the aperture providing a pathway through the base to accommodate passage of the catheter through the base and into the patient when the catheter adapter is received within the receiving channel such that the position of the catheter adapter within the receiving channel defines a depth to which the catheter extends into the patient;
a clip hingedly coupled to a proximal end of the base such that the clip pivots between an open position and a closed position, the clip having an inner surface and an outer surface, the inner surface having a second cambered surface and a second groove for retaining the catheter against the first cambered surface and the first groove when the clip is in the closed position, the outer surface configured to interlock with the receiving channel to secure the clip in the closed position.

14. The catheter system of claim 13, wherein the receiving channel is formed by a pair of opposing walls spaced to receive the catheter adapter, and wherein each wall includes an inwardly extending lip at an upper edge of the wall, a distance between the two lips being less than a width of the catheter adapter, the walls being configured to bias outwardly to enable the catheter adapter to pass between the lips and into the receiving channel, the walls further being configured to return to an unbiased position after the catheter adapter is positioned within the receiving channel such that the lips are positioned partially above the catheter adapter when the walls are in the unbiased positioned thereby maintaining the catheter adapter within the receiving channel.

15. The catheter system of claim 13, wherein the clip further comprises a pair of opposing catheter guards that are positioned distal to the catheter support when the clip is in the closed position, the catheter guards being configured to straddle a portion of the catheter when the clip is in the closed position.

* * * * *